(12) United States Patent
Ohta

(10) Patent No.: US 10,077,286 B2
(45) Date of Patent: Sep. 18, 2018

(54) METHOD FOR REMOVAL OF TRIGLYCERIDES IN LIPOPROTEINS OTHER THAN LOW-DENSITY LIPOPROTEINS

(71) Applicant: DENKA SEIKEN CO., LTD., Tokyo (JP)

(72) Inventor: Motoko Ohta, Gosen (JP)

(73) Assignee: DENKA SEIKEN CO., LTD., Tokyo (JP)

( * ) Notice: Subject to any disclaimer, the term of this patent is extended or adjusted under 35 U.S.C. 154(b) by 0 days.

(21) Appl. No.: 14/395,449

(22) PCT Filed: Apr. 19, 2013

(86) PCT No.: PCT/JP2013/061672
§ 371 (c)(1),
(2) Date: Oct. 17, 2014

(87) PCT Pub. No.: WO2013/157642
PCT Pub. Date: Oct. 24, 2013

(65) Prior Publication Data
US 2015/0132834 A1 May 14, 2015

(30) Foreign Application Priority Data
Apr. 20, 2012 (JP) .................................. 2012-097161

(51) Int. Cl.
| | |
|---|---|
| *C07K 1/14* | (2006.01) |
| *G01N 33/92* | (2006.01) |
| *G01N 33/68* | (2006.01) |
| *C12Q 1/26* | (2006.01) |
| *C12Q 1/44* | (2006.01) |
| *C12Q 1/48* | (2006.01) |
| *C12Q 1/61* | (2006.01) |

(52) U.S. Cl.
CPC .................. *C07K 1/14* (2013.01); *C12Q 1/26* (2013.01); *C12Q 1/44* (2013.01); *C12Q 1/485* (2013.01); *C12Q 1/61* (2013.01); *G01N 33/6893* (2013.01); *G01N 33/92* (2013.01); *G01N 2800/32* (2013.01); *G01N 2800/7085* (2013.01)

(58) Field of Classification Search
CPC .................................. C07K 1/14; G01N 33/92
See application file for complete search history.

(56) References Cited

U.S. PATENT DOCUMENTS

| | | | |
|---|---|---|---|
| 3,645,688 A | * 2/1972 | Smernoff | ............... G01N 33/92 436/164 |
| 6,811,994 B1 | 11/2004 | Miyauchi et al. | |
| 7,682,831 B2 | * 3/2010 | Yamamoto et al. | ............ 436/71 |
| 2004/0161811 A1 | 8/2004 | Kishi et al. | |
| 2005/0255536 A1 | 11/2005 | Okada et al. | |
| 2006/0078958 A1 | 4/2006 | Matsui | |
| 2009/0226944 A1 | 9/2009 | Katayama et al. | |

FOREIGN PATENT DOCUMENTS

| | | |
|---|---|---|
| JP | 2006-180707 A | 7/2006 |
| WO | WO 00/43537 A1 | 7/2000 |
| WO | WO 00/52480 A1 | 9/2000 |
| WO | WO 03/104486 A1 | 12/2003 |
| WO | WO 2004/055204 A1 | 7/2004 |
| WO | WO 2007/052646 A1 | 5/2007 |

OTHER PUBLICATIONS

Cholesterol esterase data sheet, 2007, 1 page.*
International Search Report, issued in PCT/JP2013/061672, dated Jul. 9, 2013.
Extended European Search Report issued in European Patent Application No. 13777616.7 dated Nov. 23, 2015.

* cited by examiner

*Primary Examiner* — Bin Shen
(74) *Attorney, Agent, or Firm* — Birch, Stewart, Kolasch & Birch, LLP

(57) ABSTRACT

Disclosed is a method for selectively eliminating triglycerides in lipoproteins other than low density lipoprotein, which method allows one to provide a method for directly and differentially quantifying LDL-TG in a sample with excellent simplicity, specificity and accuracy using an automated analyzer or the like without performing a laborious operation of pretreatment such as centrifugation or electrophoresis. The method for eliminating triglycerides in lipoproteins other than low density lipoproteins includes allowing lipoprotein lipase, cholesterol esterase, glycerol kinase and glycerol-3-phosphate oxidase to act on a sample in the presence of a surfactant that acts on lipoproteins other than low density lipoprotein and/or a surfactant having LDL-protecting action, and eliminating hydrogen peroxide produced thereby.

9 Claims, 4 Drawing Sheets

METHOD FOR REMOVAL OF TRIGLYCERIDES IN LIPOPROTEINS OTHER THAN LOW-DENSITY LIPOPROTEINS

TECHNICAL FIELD

The present invention relates to a method for eliminating triglycerides in lipoproteins other than low density lipoprotein in a sample.

BACKGROUND ART

The major components of lipids in the serum and plasma are cholesterols, triglycerides, phospholipids and the like. These blood lipids circulate in the blood as lipoproteins in which the lipids are bound to apoproteins. The lipoproteins can be classified based on their densities into chylomicron (hereinafter referred to as CM), very low density lipoprotein (hereinafter referred to as VLDL), intermediate density lipoprotein (hereinafter referred to as IDL), low density lipoprotein (hereinafter referred to as LDL), high density lipoprotein (hereinafter referred to as HDL) and the like. Among these lipoproteins, HDL has an action to transport excess cholesterol deposited in tissues to the liver, and an antiarteriosclerotic action. LDL is a major carrier in transportation of cholesterol from the liver to tissues, and an increase in LDL is considered to have a strong association with occurrence of arteriosclerosis. Thus, cholesterol in LDL (hereinafter referred to as LDL-C) is considered to be a risk factor for arteriosclerosis, ischemic heart disease (coronary artery disease)and the like, and the LDL-C content has been regarded as an important index to be known for diagnosis, therapy and prophylaxis of these diseases. On the other hand, there are also many cases where ischemic heart disease or the like has developed even with a blood LDL-C level within the normal range. Thus, recent interest has focused on changes in the quality of LDL particles, and constituents other than cholesterol.

LDL containing a large amount of triglycerides (hereinafter referred to as TG-rich LDL) are lipoprotein having properties different from those of normal LDL, which contain a large amount of cholesterols. TG-rich LDL is found in a large amount in the blood of patients with liver disease, and its blood level increases as the liver disease progresses. It is reported that TG-rich LDL accounts for a large part of lipoproteins present in the blood at the end stage of hepatic disease. TG-rich LDL causes formation of macrophage foam cells. It is reported, for example, that the rate of formation of macrophage foam cells by TG-rich LDL is directly proportional to the serum level of malondialdehyde-modified LDL, which is a type of oxidized LDL, and that, although peroxidized triglycerides can be hardly detected in the blood of healthy individuals, peroxidized triglycerides are remarkably increased in the blood of patients with liver disease. Thus, triglycerides in LDL are thought to have strong association with oxidized LDL. That is, the amount of triglycerides in LDL can be considered to be an important index associated with liver disease, and various arteriosclerosis, coronary artery disease and the like that are associated with oxidized LDL.

Examples of the method for quantifying triglycerides in LDL (hereinafter referred to as LDL-TG) include the 2-step method by the combination of operations of fractionation and triglyceride quantification. Examples of the fractionation operation include methods using ultracentrifugation, electrophoresis, high-performance liquid chromatography (HPLC) and/or the like, and examples of the quantification method include a method in which the quantification is carried out using an automated analyzer for clinical tests together with a reagent for measuring triglycerides. LDL-TG can be quantified by the combination of these, but, since the quantification is carried out in 2 steps, that is, the pretreatment step in which LDL is completely separated from the lipoproteins other than LDL and the step in which the measurement is carried out, the operations are laborious and time-consuming. Moreover, depending on the separation method, recovery of the separated sample itself may be difficult, or quantitative recovery of the sample may be difficult. Even in a method that allows quantitative recovery, the operation may require a high level of skill or a special apparatus. Thus, these methods are costly, and unlikely to be commonly employed from the viewpoint of simplicity and economy.

Known examples of methods that can solve these problems and allow measurement using an automated analyzer or the like without requiring a fractionation operation include a method in which triglycerides in all non-LDL lipoproteins are removed in the first step, and triglycerides in the remaining LDL are measured in the second step (Patent Document 1), and a method in which (free glycerol and)triglycerides in HDL are removed in the first step, and triglycerides in only LDL are measured in the second step (Patent Document 2).

However, in these methods, triglycerides in VLDL and triglycerides in CM cannot be completely removed in the first step in cases where the sample contains a large amount of these triglycerides, and the reaction proceeds also in the second step in such cases, resulting in a positive influence. Moreover, in these methods, insufficient suppression of triglycerides in VLDL, whose reaction needs to be suppressed in the second step, may cause partial promotion of the reaction, resulting in a positive influence. Although positive correlations can be actually seen when these methods are compared with the definitive method, ultracentrifugation, using a number of samples, the above methods can be seen to have serious problems in specificity and accuracy to samples, such as the existence of samples showing largely different values, and a large variation.

PRIOR ART DOCUMENTS

Patent Documents

[Patent Document 1] JP 2006-180707 A
[Patent Document 2] WO2000/043537

SUMMARY OF THE INVENTION

Problems to be Solved by the Invention

In view of this, an object of the present invention is to provide a method for selectively eliminating triglycerides in lipoproteins other than low density lipoprotein, which method allows one to provide a method for directly and differentially quantifying LDL-TG in a sample with excellent simplicity, specificity and accuracy using an automated analyzer or the like without performing a laborious operation of pretreatment such as centrifugation or electrophoresis.

Means for Solving the Problems

The present inventors discovered that allowing a certain type of surfactants in combination with a lipoprotein lipase to act on a sample causes a certain level of reaction to decompose triglycerides in non-LDL lipoproteins which are CM, VLDL, IDL and HDL, causing degradation of the triglycerides in these lipoproteins. The present inventors further considered that quantification of triglycerides in LDL can be achieved by degrading triglycerides in non-LDL lipoproteins as much as possible by increasing the selectivity and specificity, and then adding a surfactant reactive with the remaining LDL in the subsequent step to decompose the LDL, followed by degrading triglycerides in the LDL by the action of lipoprotein lipase and then quantifying the produced hydrogen peroxide. In view of this, the present inventors further studied to discover that addition of cholesterol esterase causes very selective and specific decomposition of CM, VLDL, IDL and HDL in a sample, allowing degradation of triglycerides in these non-LDL lipoprotein fractions. In order to prevent hydrogen peroxide produced as a degradation product of the triglycerides by the reaction from being detected in the subsequent step, the present inventors incorporated a hydrogen peroxide-eliminating reaction system into the above process, and, by this, succeeded in selectively eliminating the triglycerides in the lipoproteins other than low-density lipoprotein, thereby completing the present invention.

That is, the present invention provides a method for eliminating triglycerides from lipoproteins other than low density lipoprotein, the method comprising allowing lipoprotein lipase, cholesterol esterase, glycerol kinase and glycerol-3-phosphate oxidase to act on a sample in the presence of a surfactant that acts on lipoproteins other than low density lipoprotein and/or a surfactant having LDL-protecting action, and eliminating hydrogen peroxide produced thereby.

Effect of the Invention

By the method of the present invention, triglycerides in lipoproteins other than LDL can be simply eliminated without performing a laborious treatment such as centrifugation.

MODE FOR CARRYING OUT THE INVENTION

Figure 1:
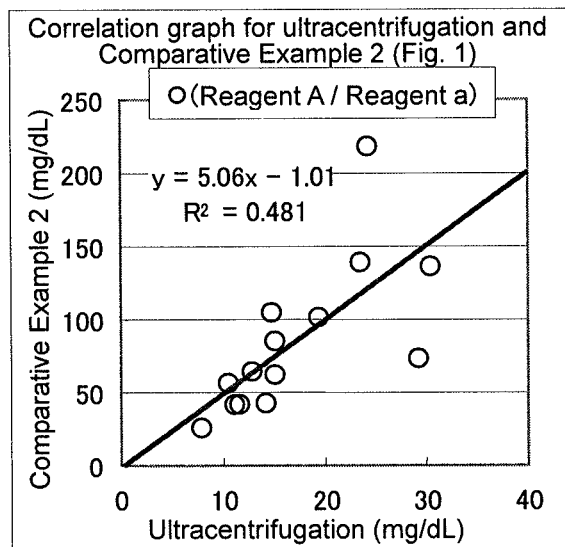
FIG. 1 is a diagram illustrating the correlation between the quantified value of triglycerides in LDL as determined by ultracentrifugation and the quantified value of triglycerides in LDL as determined by the method of Comparative Example 2.

The method of the present invention eliminates triglycerides in non-LDL lipoproteins in a sample by the method described below. Examples of the non-LDL lipoproteins include CM, VLDL, IDL and HDL. Since the triglycerides in CM, VLDL, IDL and HDL are eliminated, triglycerides quantified by degradation of lipoproteins in the subsequent step are mainly triglycerides in LDL in the sample.

The sample to be subjected to the method of the present invention is not limited as long as it is a sample that potentially contains a lipoprotein(s) such as CM, VLDL, IDL, LDL, HDL and/or the like. Examples of the sample include, but are not limited to, body fluids such as blood, serum and plasma, and dilutions thereof.

The "elimination of triglycerides" in the present invention means to degrade triglycerides and to prevent their degradation products from being detected in the subsequent step. Examples of methods that may be carried out for selectively eliminating triglycerides contained in non-LDL lipoproteins, that is, CM, VLDL, IDL, HDL and the like, include the following methods.

That is, in the presence of a surfactant that acts on non-LDL lipoproteins, or a surfactant having LDL-protecting action, lipoprotein lipase, cholesterol esterase, glycerol kinase and glycerol-3-phosphate oxidase are allowed to act on the sample, and hydrogen peroxide produced thereby is eliminated.

Examples of the method for eliminating hydrogen peroxide include a method in which catalase is allowed to act on the hydrogen peroxide to cause its degradation into water and oxygen, and a method in which peroxidase is used to allow reaction of a phenol-based or aniline-based hydrogen donor compound with hydrogen peroxide to cause conversion of the hydrogen peroxide into colorless quinone. Either method may be used, and the method is not limited to these methods. These methods per se for elimination of hydrogen peroxide are well known in the art.

The concentration of the lipoprotein lipase in the reaction liquid is preferably about 0.01 to 2000 KU/L, more preferably about 0.05 to 1000 KU/L. The concentration of the glycerol kinase is preferably about 0.02 to 80.0 KU/L, more preferably about 0.05 to 40.0 KU/L. The concentration of the glycerol-3-phosphate oxidase is preferably about 0.2 to 20.0 KU/L, more preferably about 0.5 to 10.0 KU/L. The concentration of the catalase in the cases of degradation of hydrogen peroxide to water and oxygen is preferably about 40 to 5000 KU/L, more preferably about 50 to 2000 KU/L.

The concentration of the peroxidase in the cases of conversion of hydrogen peroxide in the reaction liquid into colorless quinone is preferably 1 to 40 KU/L, more preferably 2 to 30 KU/L. The concentration of the phenol-based or aniline-based hydrogen donor compound to be added in such cases is preferably 0.2 to 3 mmol/L.

Preferred examples of the cholesterol esterase to be used in the method of the present invention include cholesterol esterase having a molecular weight of not more than 50 kDa. Even in cases where a cholesterol esterase has a molecular weight of not less than 50 kDa, the cholesterol esterase is preferred if the cholesterol esterase has a subunit with a molecular weight of not more than 50 kDa. The origin of the cholesterol esterase is not limited, and may be derived from any animal or microorganism. A cholesterol esterase derived from *Pseudomonas* sp. may be especially preferably used.

The concentration of the cholesterol esterase to be used in the method of the present invention is preferably about 10 to 8000 U/L, more preferably about 50 to 4000 U/L.

Preferred examples of the surfactant that acts on non-LDL lipoproteins, or surfactant having LDL-protecting action, to be used in the method of the present invention include polyoxyalkylene derivatives having an HLB value of 13 to 15. Examples of the derivatives include condensates with a higher alcohol, condensates with a higher fatty acid, condensates with a higher fatty acid amide, condensates with a higher alkylamine, condensates with a higher alkylmercaptane, and condensates with an alkylphenol.

Preferred specific examples of the polyoxyalkylene derivatives having an HLB value of 13 to 15 include, but are not limited to, polyoxyethylene lauryl ether, polyoxyethylene cetyl ether, polyoxyethylene oleyl ether, polyoxyethylene higher alcohol ether, polyoxyethylene octyl phenyl ether, polyoxyethylene nonylphenyl ether, polyoxyethylene benzyl phenyl ether and polyoxyalkylene polycyclic phenyl ether.

As the surfactant to be used in the method of the present invention, a cationic surfactant may be used. Examples of the cationic surfactant to be used herein include, but are not limited to, those having a quaternary ammonium salt as a hydrophilic group. The surfactant may be a single type of surfactant, or may be a combination of 2 or more types of surfactants.

The surfactant is used at a concentration of preferably about 0.01 to 20 g/L, more preferably about 0.1 to 10 g/L.

The method of the present invention is preferably carried out in a buffer at a pH of 5 to 9. The buffer is preferably a buffer containing an amine, such as a Tris, triethanolamine or Good's buffer. Preferred examples of the buffer include Bis-Tris, PIPES, MOPSO, BES, HEPES and POPSO, which are Good's buffers. The concentration of the buffer is preferably about 5 to 5000 mM, more preferably about 10 to 1000 mM.

In the method of the present invention, a divalent metal ion may be included in the reaction liquid in order to suppress the reaction with LDL to further increase the elimination of other lipoproteins, or in order to strengthen and stabilize the activities/actions of enzymes in the reaction liquid. Copper ion, iron ion, calcium ion or magnesium ion may be used as the divalent metal ion, and magnesium ion is especially preferred. The concentration of the divalent metal ion is preferably about 1 to 500 mM, more preferably about 5 to 200 mM.

The reaction temperature is, for example, 15 to 55° C., suitably about 25 to 45° C., most preferably 37° C. The reaction time may be about 1 to 30 minutes, more preferably about 2 to 15 minutes.

In the method of the present invention, albumin may be added in order to prevent interference of a residual product with the reaction with LDL. By performing the reaction in the presence of albumin, a residual product produced as a result of the reaction is adsorbed by the albumin, and interference of the residual product with the reaction in the subsequent step can be prevented. The albumin is not limited, and a commercially available albumin may be preferably used. The origin of the albumin is also not limited, and may be any animal such as human, cattle, pig or horse. Bovine serum albumin, which is widely used, may be especially preferably used. The concentration of the albumin in the reaction solution is preferably 0.01 to 30.0 g/L, more preferably 0.3 to 20.0g/L.

In the method of the present invention, the surfactant; the enzymes that act on non-LDL lipoproteins and degrade these lipoproteins, composed of lipoprotein lipase, cholesterol esterase, glycerol kinase and glycerol-3-phosphate oxidase; and the enzyme for eliminating hydrogen peroxide, such as catalase; may be added either simultaneously or separately. Preferably, a reagent containing all of these reagents is prepared, and the prepared reagent is mixed with the sample.

By the method of the present invention described above, triglycerides in non-LDL lipoproteins are selectively eliminated. Therefore, in the subsequent step, triglycerides in LDL can be quantified by degrading lipoproteins and quantifying triglycerides.

The quantification can be carried out by, for example, adding a surfactant that acts at least on LDL and quantifying hydrogen peroxide produced by the actions of lipoprotein lipase, glycerol kinase and glycerol-3-phosphate oxidase remaining in the reaction system after carrying out the method of the present invention. These enzymes necessary for the quantification may be further added in addition to the enzymes that have been added in the method of the present invention and are remaining in the reaction system. Both in the method of the present invention and in the subsequent step, each of the enzymes to be involved in the reaction is not limited to a single type of enzyme, and 2 or more types of enzymes may be used in combination.

The surfactant that acts at least on LDL in the subsequent step may be either a surfactant that selectively acts on LDL, or a surfactant that acts on all lipoproteins.

Preferred examples of the surfactant that acts on all lipoproteins include polyoxyalkylene derivatives having an HLB value of not less than 11, preferably not less than 12. Examples of the derivatives include condensates with a higher alcohol, condensates with a higher fatty acid, condensates with a higher fatty acid amide, condensates with a higher alkylamine, condensates with a higher alkylmercaptane, and condensates with an alkylphenol.

Preferred specific examples of the polyoxyalkylene derivatives having an HLB value of not less than 11 include, but are not limited to, polyoxyethylene lauryl ether, polyoxyethylene cetyl ether, polyoxyethylene oleyl ether, polyoxyethylene higher alcohol ether, polyoxyethylene octyl phenyl ether, polyoxyethylene nonylphenyl ether and polyoxyethylene polycyclic phenyl ether; and polyoxyalkylene polycyclic phenyl ethers having an HLB value of less than 13.

Examples of the surfactant that selectively acts on LDL include anionic surfactants and carboxybetaine amphoteric surfactants. Examples of the anionic surfactant to be used herein include, but are not limited to, those containing an aromatic ring having a $C_4$-$C_{18}$ linear or branched alkyl group bound thereto; those in which the aromatic ring is composed of only carbon and hydrogen, and constitutes benzene, naphthalene, diphenyl or the like; and those in which the aromatic ring has a hydrophilic group such as a sulfonate group bound thereto.

The concentration of the surfactant to be used in the subsequent step is preferably about 0.1 to 100 g/L, more preferably about 1 to 50 g/L. As the surfactant, a single type of surfactant may be used, or 2 or more types of surfactants may be used in combination.

Other preferred reaction conditions in the subsequent step are the same as the preferred reaction conditions in the first step.

The quantification of the produced hydrogen peroxide can be carried out by a conventional method. For example, oxidative condensation may be allowed to occur between 4-aminoantipyrine and a phenol-based or aniline-based hydrogen donor compound in the presence of hydrogen peroxide by the action of peroxidase, followed by quantification of a pigment produced thereby. Examples of the phenol-based or aniline-based hydrogen donor compound include N-(2-hydroxy-3-sulfopropyl)-3,5-dimethoxyaniline (HDAOS), N-ethyl-N-(2-hydroxy-3-sulfopropyl)-3-methoxyaniline (TOOS) and N-ethyl-N-(3-methylphenyl)-N'-succinylethylenediamine (EMSE).

The present invention is described below concretely by way of Examples. However, the present invention is not limited to the Examples below.

EXAMPLES

Comparative Example 1

The LDL-TG quantification reagents having the following compositions were prepared.
First Reagent (Reagent A)

| | |
|---|---|
| PIPES buffer (pH 6.5) | 50 mmol/L |
| Surfactant*1 | 2.0 g/L |
| Bovine serum albumin | 3.0 g/L |
| Trinder Reagent (TOOS) | 0.5 g/L |
| Magnesium chloride | 4.0 g/L |
| Glycerol kinase | 3.0 KU/L |
| Glycerol-3-phosphate oxidase | 7.5 KU/L |
| Lipoprotein lipase | 100 KU/L |
| Catalase | 1000 KU/L |

*1Polyoxyalkylene derivative (HLB value, 13.2)

Second Reagent (Reagent a)

| | |
|---|---|
| PIPES buffer (pH 7.0) | 50 mmol/L |
| Surfactant*2 | 6.0 g/L |
| 4-Aminoantipyrine | 4.0 mmol/L |
| Lipoprotein lipase | 5.0 KU/L |
| Peroxidase | 5.0 KU/L |
| Sodium azide | 0.05% |

*2Polyoxyethylene alkyl ether (HLB value, 13.3)

Example 1

The LDL-TG quantification reagents having the following compositions were prepared.
First Reagent (Reagent B)

| | |
|---|---|
| PIPES buffer (pH 6.5) | 50 mmol/L |
| Surfactant*3 | 2.0 g/L |
| Bovine serum albumin | 3.0 g/L |
| Trinder Reagent (TOOS) | 0.5 g/L |
| Magnesium chloride | 4.0 g/L |
| Glycerol kinase | 2.0 KU/L |
| Glycerol-3-phosphate oxidase | 7.5 KU/L |
| Lipoprotein lipase | 100 KU/L |
| Cholesterol esterase#1 | 0.6 KU/L |
| Catalase | 1000 KU/L |

*3Polyoxyalkylene derivative (HLB value, 13.2)
1About 30 kDa (derived from *Pseudomonas* sp.)

Second Reagent (Reagent a)

| | |
|---|---|
| PIPES buffer (pH 7.0) | 50 mmol/L |
| Surfactant*4 | 6.0 g/L |
| 4-Aminoantipyrine | 4.0 mmol/L |
| Lipoprotein lipase | 5.0 KU/L |
| Peroxidase | 5.0 KU/L |
| Sodium azide | 0.05% |

*4Polyoxyethylene alkyl ether (HLB value, 13.3)

Example 2

The LDL-TG quantification reagents having the following compositions were prepared.
First Reagent (Reagent C)

| | |
|---|---|
| PIPES buffer (pH 6.5) | 50 mmol/L |
| Surfactant*5 | 2.0 g/L |
| Bovine serum albumin | 3.0 g/L |
| Trinder Reagent (TOOS) | 0.5 g/L |
| Magnesium chloride | 4.0 g/L |
| Glycerol kinase | 1.0 KU/L |
| Glycerol-3-phosphate oxidase | 4.0 KU/L |
| Lipoprotein lipase | 0.3 KU/L |
| Cholesterol esterase#2 | 0.7 KU/L |
| Catalase | 1000 KU/L |

*5Polyoxyalkylene derivative (HLB value, 13.2)
2About 30 kDa (derived from *Pseudomonas* sp.)

Second Reagent (Reagent b)

| | |
|---|---|
| PIPES buffer (pH 7.0) | 50 mmol/L |
| Surfactant*6 | 6.0 g/L |
| 4-Aminoantipyrine | 4.0 mmol/L |
| Lipoprotein lipase | 400 KU/L |
| Peroxidase | 5.0 KU/L |
| Sodium azide | 0.05% |

*6Polyoxyethylene alkyl ether (HLB value, 12.4)

Example 3

In terms of the samples to used for the evaluation, a fraction containing both CM and VLDL (specific gravity, from less than 0.96 to 1.006) or fraction containing all of CM, VLDL and IDL (specific gravity, from less than 0.96 to 1.019), LDL fraction (specific gravity, from 1.019 to 1.063) and HDL fraction (specific gravity, from 1.063 to 1.210)are separated using, for example, ultracentrifugation. Each of these fraction samples was subjected to measurement of the total amount of triglycerides, and the measured amount was compared with the amounts of triglycerides quantified using the reagents of the above Examples. The ultracentrifugation was carried out according to the method described in "New Biochemistry Experiment Lecture 4: Lipid I—Neutral Lipids and Lipoproteins", Tokyo Kagaku Dojin Publishing Company.

The reagents of Comparative Example 1, Example 1 and Example 2 were subjected to the following operations. After taking 2 μL of the sample, 195 μL of the first reagent was mixed therewith, and the resulting mixture was warmed at 37° C. for 5 minutes to allow the reaction to proceed, followed by measurement of the absorbance (E1) of the reaction liquid at a primary wavelength of 600 nm and at a secondary wavelength of 700 nm. Subsequently, 65 μL of the second reagent was mixed with this reaction liquid, and the resulting mixture was further heated at 37° C. for 5 minutes to allow the reaction to proceed, followed by measurement of the absorbance (E2) of the reaction liquid at a primary wavelength of 600 nm and at a secondary wavelength of 700 nm. By subtracting the measured absorbance E1 from the measured absorbance E2, the amount of change in the absorbance (ΔE) was calculated. The reaction absorbance in each lipoprotein fraction sample after use of reagents of the present Example can be calculated by subtracting the amount of change in the absorbance observed using physiological saline or the like instead of the lipoprotein fraction sample, from the amount of change in the absorbance observed using the lipoprotein fraction sample. In this process, the measurement of the sample can be carried out without any problem even in cases where the second reagent (Reagent a) in Comparative Example 1 or Example 1 is replaced by the second reagent of Example 2 (Reagent b).

The same operation was carried out using a reagent for measuring total triglycerides that exhibits equivalent coloration, instead of the reagents of the present Example. The reaction absorbance calculated thereby corresponds to the total amount of triglycerides in each lipoprotein fraction sample, and, by comparing this reaction absorbance with the reaction absorbance observed using the reagents of the present Example for each lipoprotein fraction sample, the reaction rate of the reagents of the present Example in each sample can be calculated. The term "comparing the reaction absorbance corresponding to the total amount of triglycerides with the reaction absorbance observed using the reagents of the present Example"herein means, for example, dividing the reaction absorbance observed using the reagents of the present Example by the reaction absorbance corresponding to the total amount of triglycerides". Examples of the reagent for measuring total triglycerides that exhibits equivalent coloration include TG-EX "Seiken" (enzyme method) (Triglyceride Kit).

The reaction rates calculated by this process are summarized in the table below.

TABLE 1

| Fractionated sample | | Comparative Example 1 | Example 1 | Example 2 |
| --- | --- | --- | --- | --- |
| CM/VLDL fraction | Sample 1 | 100% | 1% | 1% |
| | Sample 2 | 102% | 1% | 1% |
| CM/VLDL/IDL fraction | Sample 3 | 100% | 1% | 1% |
| | Sample 4 | 99% | 1% | 1% |
| LDL fraction | Sample 5 | 95% | 63% | 62% |
| | Sample 6 | 97% | 72% | 70% |
| | Sample 7 | 99% | 64% | 61% |
| HDL fraction | Sample 8 | 8% | 4% | 3% |
| | Sample 9 | 8% | 4% | 3% |
| | Sample 10 | 12% | 6% | 5% |

It can be seen, in Example 1 and Example 2,that the reaction occurred specifically in the LDL fraction, and that differentiation of the LDL fraction from the CM fraction, VLDL fraction, IDL fraction and HDL fraction was successful. In Comparative Example 1, triglycerides were not eliminated, or the reaction was not suppressed, in the CM fraction, VLDL fraction and IDL fraction. Although, in Comparative Example 1, the elimination was achieved or the reaction was suppressed in the HDL fraction, it can be seen that Example 1 and Example 2 gave better results on specificity. The total amount of triglycerides in each of these fractions was: about 450 to 950 mg/dL in the CM/VLDL fraction or CM/VLDL/IDL fraction; about 50 to 220 mg/dL in the LDL fraction; and 35 to 80 mg/dL in the HDL fraction.

Subsequently, fresh human serum samples were subjected to quantification of LDL-TG in each of the samples by ultracentrifugation, or by using the reagents of the present invention.

Example 4

(1) Quantification Measurement of LDL-TG by Ultracentrifugation

Ultracentrifugation was carried out by performing centrifugation according to a conventional method (the method described in "New Biochemistry Experiment Lecture 4: Lipid I—Neutral Lipids and Lipoproteins", Tokyo Kagaku Dojin Publishing Company) to obtain an LDL fraction within the specific gravity range of 1.019 to 1.063, and the amount of triglycerides in the obtained LDL fraction was measured using TG-EX "Seiken" (enzyme method) (manufactured by Denka Seiken Co., Ltd.).

Comparative Example 2

Using a human serum sample, and the combination of Reagent A and Reagent a having the same compositions as in the Comparative Example 1, the following operations were carried out.

(2) Quantification Measurement of LDL-TG by Use of Reagents of Present Invention After taking 2 μL of the sample, 195 μL of the first reagent was mixed therewith, and the resulting mixture was warmed at 37° C. for 5 minutes to allow the reaction to proceed, followed by measurement of the absorbance (E1) of the reaction liquid at a primary wavelength of 600 nm and at a secondary wavelength of 700 nm. Subsequently, 65 μL of the second reagent was mixed with this reaction liquid, and the resulting mixture was further heated at 37° C. for 5 minutes to allow the reaction to proceed, followed by measurement of the absorbance (E2) of the reaction liquid at a primary wavelength of 600 nm and at a secondary wavelength of 700 nm. By subtracting the measured absorbance E1 from the measured absorbance E2, the amount of change in the absorbance (ΔE) was calculated. The reaction absorbance in the human serum sample after the use of the reagents of the present Example was calculated by subtracting the amount of change in the absorbance observed using physiological saline or the like instead of the human serum sample, from the amount of change in the absorbance observed using the human serum sample.

(3) Preparation of Calibration Curve

A calibration curve was prepared by using several fresh human serum standard samples containing LDL-TG at known concentrations, which were determined by ultracentrifugation measurement. The reaction absorbance calculated in (2) was converted into mg/dL measurement value.

Example 5

Using human serum-01 to human serum-14 as samples together with the combination of Reagent B and Reagent a having the same compositions as in the Example 1,the same operations as described in the (2) and (3) were carried out.

Example 6

Using human serum-01 to human serum-14 as samples together with the combination of Reagent C and Reagent b having the same compositions as in the Example 2, the same operations as described in the (2) and (3) were carried out.

Example 7

The LDL-TG quantification reagents having the following compositions were prepared.
First Reagent (Reagent D)

| | |
|---|---|
| PIPES buffer (pH 6.5) | 50 mmol/L |
| Surfactant*7 | 2.5 g/L |
| Bovine serum albumin | 3.0 g/L |
| Trinder Reagent (TOOS) | 0.5 g/L |
| Magnesium chloride | 4.0 g/L |
| Glycerol kinase | 1.0 KU/L |
| Glycerol-3-phosphate oxidase | 4.0 KU/L |
| Lipoprotein lipase | 100 KU/L |
| Cholesterol esterase#3 | 6.0 KU/L |
| Catalase | 1000 KU/L |

*7Polyoxyalkylene derivative (HLB value, 13.2)
3Unknown molecular weight (microbial origin, according to the manufacturer)

Second Reagent (Reagent c)

| | |
|---|---|
| PIPES buffer (pH 7.0) | 50 mmol/L |
| Surfactant*8 | 6.0 g/L |
| 4-Aminoantipyrine | 4.0 mmol/L |
| Lipoprotein lipase | 400 KU/L |
| Peroxidase | 5.0 KU/L |
| Sodium azide | 0.05% |

*8Polyoxyethylene alkyl ether (HLB value, 12.4)

Using human serum-01 to human serum-14 as samples together with the combination of Reagent D and Reagent c, the same operations as described in the (2) and (3) were carried out.

Figure 2:
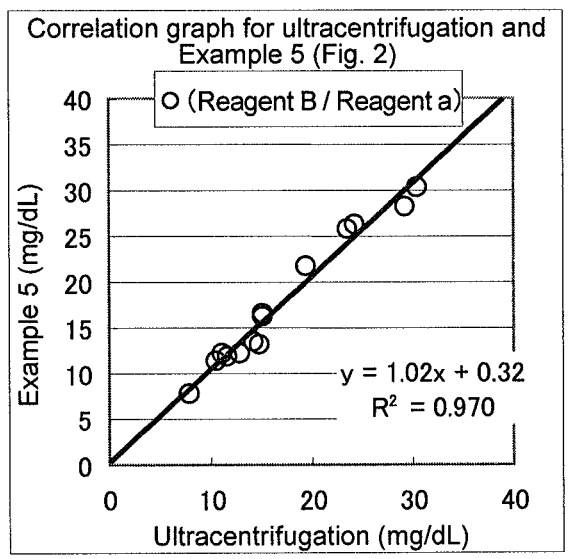
FIG. 2 is a diagram illustrating the correlation between the quantified value of triglycerides in LDL as determined by ultracentrifugation and the quantified value of triglycerides in LDL as determined by the method of Example 5.
Figure 3:
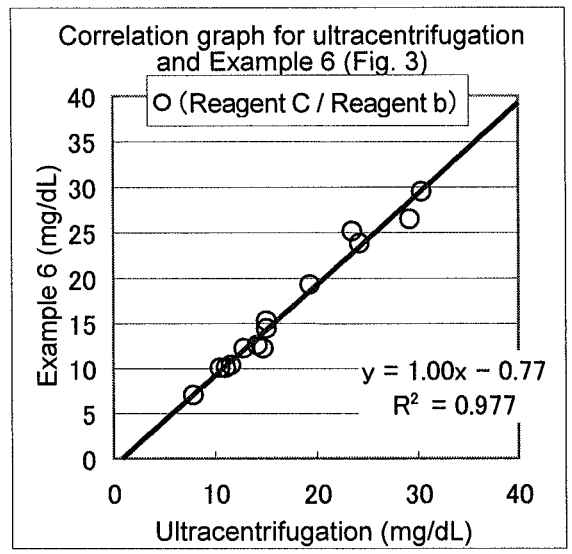
FIG. 3 is a diagram illustrating the correlation between the quantified value of triglycerides in LDL as determined by ultracentrifugation and the quantified value of triglycerides in LDL as determined by the method of Example 6.
Figure 4:
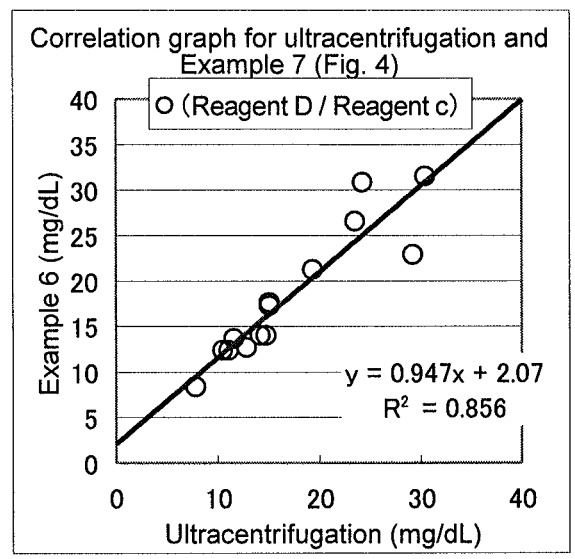
FIG. 4 is a diagram illustrating the correlation between the quantified value of triglycerides in LDL as determined by ultracentrifugation and the quantified value of triglycerides in LDL as determined by the method of Example 7.

The LDL-TG measurement values (mg/dL) calculated for the 14 human serum samples, human serum-01 to human serum-14, according to the (1) after the ultracentrifugation in Example 4; and the LDL-TG measurement values (mg/dL) calculated according to the (2) and (3) in Comparative Example 2, Example 5, Example 6 and Example 7, and their correlation graphs; are shown below in Table 2, FIG. 1, FIG. 2, FIG. 3 and FIG. 4.

In terms of correlation with Example 4, the square of the correlation coefficient was 0.481 in Comparative Example 2, while the square of the correlation coefficient was 0.970 in Example 5, 0.977 in Example 6, and 0.856 in Example 7.

It can be seen that the values obtained by the Examples in the present invention show evidently higher correlation with those obtained by the ultracentrifugation in Example 4, which is known to be capable of accurate measurement, as compared to Comparative Example 2.

Comparative Example 3

The LDL-TG quantification reagents having the following compositions were prepared.
First Reagent (Reagent A)

| | |
|---|---|
| PIPES buffer (pH 6.5) | 50 mmol/L |
| Surfactant*9 | 2.0 g/L |
| Bovine serum albumin | 3.0 g/L |
| Trinder Reagent (TOOS) | 0.5 g/L |
| Magnesium chloride | 4.0 g/L |
| Glycerol kinase | 3.0 KU/L |
| Glycerol-3-phosphate oxidase | 7.5 KU/L |
| Lipoprotein lipase | 100 KU/L |
| Catalase | 1000 KU/L |

*9Polyoxyalkylene derivative (HLB value, 13.2)

Second Reagent (Reagent d)

| | |
|---|---|
| PIPES buffer (pH 7.0) | 50 mmol/L |
| Surfactant*10 | 6.0 g/L |
| 4-Aminoantipyrine | 4.0 mmol/L |
| Peroxidase | 10.0 KU/L |
| Sodium azide | 0.05% |

*10Polyoxyethylene alkyl ether (HLB value, 13.3)

Using human serum-15 to human serum-30 as samples together with the combination of Reagent A and Reagent d, the same operations as described in the (2) and (3) were carried out.

Example 8

The LDL-TG quantification reagents having the following compositions were prepared.

TABLE 2

| | LDL-TG measurement value | | | | |
|---|---|---|---|---|---|
| Sample | Example 4 (ultracentrifugation) | Comparative Example 2 (Reagent A/ Reagent a) | Example 5 (Reagent B/ Reagent a) | Example 6 (Reagent C/ Reagent b) | Example 7 (Reagent D/ Reagent c) |
| Human serum-01 | 7.8 | 26.0 | 7.9 | 7.1 | 8.4 |
| Human serum-02 | 19.3 | 101.8 | 21.8 | 19.3 | 21.3 |
| Human serum-03 | 10.5 | 56.8 | 11.4 | 10.1 | 12.4 |
| Human serum-04 | 12.8 | 64.5 | 12.2 | 12.3 | 12.7 |
| Human serum-05 | 14.8 | 105.1 | 13.2 | 12.3 | 14.0 |
| Human serum-06 | 14.2 | 42.8 | 13.5 | 12.6 | 14.0 |
| Human serum-07 | 15.1 | 62.4 | 16.6 | 15.3 | 17.3 |
| Human serum-08 | 11.6 | 42.1 | 11.9 | 10.4 | 13.7 |
| Human serum-09 | 11.1 | 41.7 | 12.2 | 10.1 | 12.4 |
| Human serum-10 | 15.1 | 85.6 | 16.3 | 14.4 | 17.7 |
| Human serum-11 | 24.2 | 218.7 | 26.3 | 23.9 | 30.9 |
| Human serum-12 | 29.2 | 73.6 | 28.3 | 26.5 | 22.9 |
| Human serum-13 | 23.5 | 139.4 | 25.8 | 25.2 | 26.6 |
| Human serum-14 | 30.4 | 136.4 | 30.4 | 29.6 | 31.5 |

Unit: mg/dL

First Reagent (Reagent F)

| PIPES buffer (pH 6.5) | 50 mmol/L |
|---|---|
| Surfactant*11 | 2.0 g/L |
| Bovine serum albumin | 10.0 g/L |
| Trinder Reagent (TOOS) | 0.5 g/L |
| Magnesium chloride | 1.5 g/L |
| Glycerol kinase | 1.0 KU/L |
| Glycerol-3-phosphate oxidase | 4.0 KU/L |
| Lipoprotein lipase | 100 KU/L |
| Cholesterol esterase#4 | 0.7 KU/L |
| Catalase | 1000 KU/L |

*11Polyoxyalkylene derivative (HLB value, 13.2)
4About 30 kDa (derived from *Pseudomonas* sp.)

Second Reagent (Reagent d)

| PIPES buffer (pH 7.0) | 50 mmol/L |
|---|---|
| Surfactant*12 | 6.0 g/L |
| 4-Aminoantipyrine | 4.0 mmol/L |
| Peroxidase | 10.0 KU/L |
| Sodium azide | 0.05% |

*12Polyoxyethylene alkyl ether (HLB value, 13.3)

Using human serum-15 to human serum-30 as samples together with the combination of Reagent F and Reagent d, the same operations as described in the (2) and (3) were carried out.

Example 9

The LDL-TG quantification reagents having the following compositions were prepared.
First Reagent (Reagent G)

| PIPES buffer (pH 6.5) | 50 mmol/L |
|---|---|
| Surfactant*13 | 1.5 g/L |
| Bovine serum albumin | 10.0 g/L |
| Trinder Reagent (TOOS) | 0.5 g/L |
| Magnesium chloride | 1.5 g/L |
| Glycerol kinase | 1.0 KU/L |
| Glycerol-3-phosphate oxidase | 4.0 KU/L |
| Lipoprotein lipase | 100 KU/L |
| Cholesterol esterase#5 | 1.5 KU/L |
| Catalase | 1000 KU/L |

*13Polyoxyalkylene derivative (HLB value, 13.2)
5About 300 kDa (*Pseudomonas* sp.-derived, according to the manufacturer) (bands of about 60 kDa and about 30 kDa were found by SDS-PAGE)

Second Reagent (Reagent d)

| PIPES buffer (pH 7.0) | 50 mmol/L |
|---|---|
| Surfactant*14 | 6.0 g/L |
| 4-Aminoantipyrine | 4.0 mmol/L |
| Peroxidase | 10.0 KU/L |
| Sodium azide | 0.05% |

*14Polyoxyethylene alkyl ether (HLB value, 13.3)

Using human serum-15 to human serum-30 as samples together with the combination of Reagent G and Reagent d, the same operations as described in the (2) and (3) were carried out.

Example 10

The LDL-TG quantification reagents,having the following compositions were prepared.
First Reagent (Reagent H)

| PIPES buffer (pH 6.5) | 50 mmol/L |
|---|---|
| Surfactant*15 | 1.5 g/L |
| Bovine serum albumin | 10.0 g/L |
| Trinder Reagent (TOOS) | 0.5 g/L |
| Magnesium chloride | 1.5 g/L |
| Glycerol kinase | 1.0 KU/L |
| Glycerol-3-phosphate oxidase | 4.0 KU/L |
| Lipoprotein lipase | 100 KU/L |
| Cholesterol esterase#6 | 1.5 KU/L |
| Catalase | 1000 KU/L |

*15Polyoxyalkylene derivative (HLB value, 13.2)
6Unknown molecular weight (microorganism-derived, according to the manufacturer) (bands of about 70 kDa and about 30 kDa were found by SDS-PAGE)

Second Reagent (Reagent d)

| PIPES buffer (pH 7.0) | 50 mmol/L |
|---|---|
| Surfactant*16 | 6.0 g/L |
| 4-Aminoantipyrine | 4.0 mmol/L |
| Peroxidase | 10.0 KU/L |
| Sodium azide | 0.05% |

*16Polyoxyethylene alkyl ether (HLB value, 13.3)

Using human serum-15 to human serum-30 as samples together with the combination of Reagent H and Reagent d, the same operations as described in the (2) and (3) were carried out.

Figure 5:
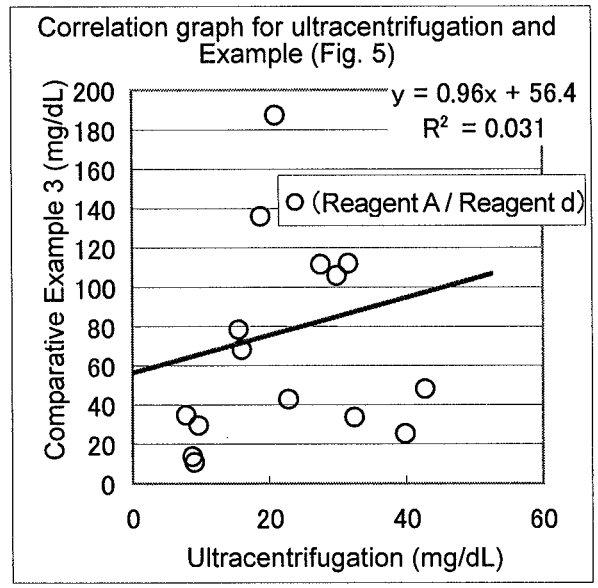
FIG. 5 is a diagram illustrating the correlation between the quantified value of triglycerides in LDL as determined by ultracentrifugation and the quantified value of triglycerides in LDL as determined by the method of Comparative Example 3.
Figure 6:
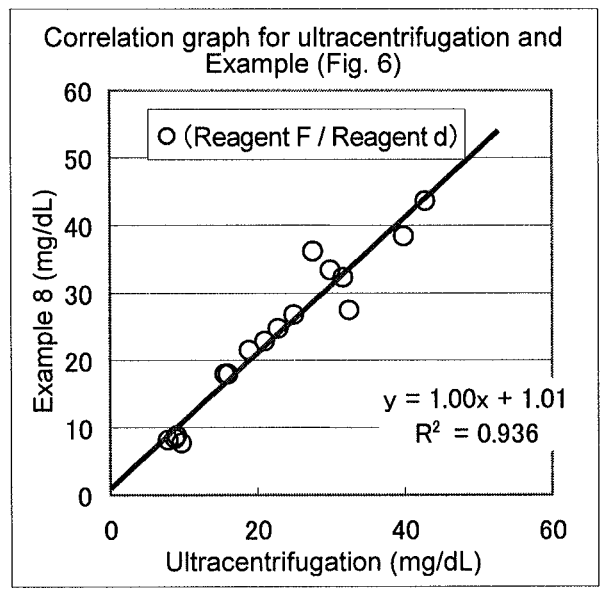
FIG. 6 is a diagram illustrating the correlation between the quantified value of triglycerides in LDL as determined by ultracentrifugation and the quantified value of triglycerides in LDL as determined by the method of Example 8.
Figure 7:
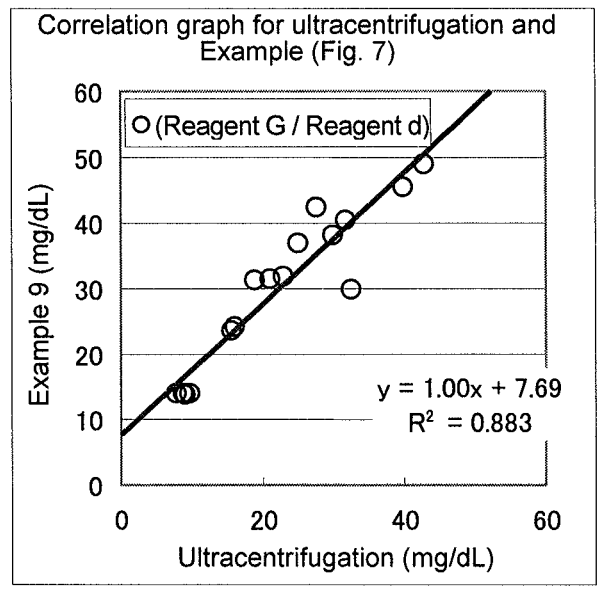
FIG. 7 is a diagram illustrating the correlation between the quantified value of triglycerides in LDL as determined by ultracentrifugation and the quantified value of triglycerides in LDL as determined by the method of Example 9.
Figure 8:
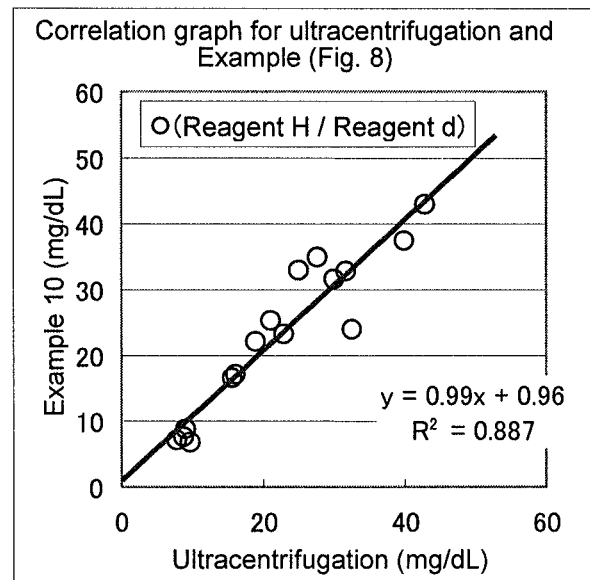
FIG. 8 is a diagram illustrating the correlation between the quantified value of triglycerides in LDL as determined by ultracentrifugation and the quantified value of triglycerides in LDL as determined by the method of Example 10.

The LDL-TG measurement values (mg/dL) calculated for the 16 human serum samples, human serum-15 to human serum-30, according to the (1); and the LDL-TG measurement values (mg/dL) calculated according to the (2) and (3) in Comparative Example 3, Example 8, Example 9 and Example 10, and their correlation graphs; are shown below in Table 3, FIG. 5, FIG. 6, FIG. 7 and FIG. 8.

TABLE 3

| | LDL-TG (mg/dL) | | | | |
|---|---|---|---|---|---|
| Sample | Example 4 (ultracentrifugation) | Comparative Example 3 (Reagent A/ Reagent d) | Example 8 (Reagent F/ Reagent d) | Example 9 (Reagent G/ Reagent d) | Example 10 (Reagent H/ Reagent d) |
| Human serum-15 | 15.6 | 78.6 | 18.0 | 22.7 | 16.7 |
| Human serum-16 | 31.7 | 112.1 | 32.3 | 38.8 | 32.8 |
| Human serum-17 | 9.0 | 10.9 | 8.8 | 13.3 | 8.8 |
| Human serum-18 | 21.0 | 187.4 | 22.8 | 30.3 | 25.3 |
| Human serum-19 | 9.7 | 29.4 | 7.7 | 13.5 | 6.8 |
| Human serum-20 | 25.0 | 207.5 | 26.8 | 35.5 | 33.0 |
| Human serum-21 | 7.8 | 34.6 | 8.2 | 13.5 | 7.2 |
| Human serum-22 | 8.8 | 13.7 | 8.4 | 13.5 | 7.7 |
| Human serum-23 | 27.6 | 111.6 | 36.2 | 40.8 | 35.0 |

TABLE 3-continued

| | | LDL-TG (mg/dL) | | | |
|---|---|---|---|---|---|
| Sample | Example 4 (ultracentrifugation) | Comparative Example 3 (Reagent A/ Reagent d) | Example 8 (Reagent F/ Reagent d) | Example 9 (Reagent G/ Reagent d) | Example 10 (Reagent H/ Reagent d) |
| Human serum-24 | 16.0 | 68.3 | 18.0 | 23.3 | 17.2 |
| Human serum-25 | 18.9 | 136.2 | 21.5 | 30.1 | 22.2 |
| Human serum-26 | 29.9 | 105.9 | 33.4 | 36.7 | 31.7 |
| Human serum-27 | 22.9 | 42.8 | 24.7 | 30.7 | 23.3 |
| Human serum-28 | 32.5 | 33.8 | 27.5 | 28.7 | 24.0 |
| Human serum-29 | 42.8 | 48.0 | 43.6 | 47.0 | 43.0 |
| Human serum-30 | 39.9 | 25.3 | 38.4 | 43.7 | 37.5 |

Unit: mg/dL

In terms of correlation with Example 4, the square of the correlation coefficient was 0.031 in Comparative Example 3, while the square of the correlation coefficient was 0.936 in Example 8, 0.883 in Example 9, and 0.887 in Example 10.

It can be seen that the values obtained by the Examples in the present invention show evidently higher correlation with those obtained by the ultracentrifugation in Example 4, which is known to be capable of accurate measurement, as compared to Comparative Example 3.

The invention claimed is:

1. A method for specifically qualifying triglycerides in low density lipoprotein, said method comprising:
  eliminating triglycerides in non-LDL lipoproteins by allowing lipoprotein lipase, cholesterol esterase, glycerol kinase and glycerol-3-phosphate oxidase to simultaneously act on a sample in the presence of a surfactant that acts on lipoproteins other than low density lipoprotein and/or a surfactant having LDL-protecting action;
  eliminating hydrogen peroxide produced thereby; and
  specifically quantifying triglycerides in low density lipoprotein.

2. The method according to claim 1, wherein said surfactant is a polyoxyalkylene derivative having a Hydrophile-Lipophile Balance (HLB) value of 13 to 15.

3. The method according to claim 2, wherein said polyoxyalkylene derivative is a polyoxyalkylene polycyclic phenylether having an HLB value of 13 to 15.

4. The method according to claim 2, wherein said polyoxyalkylene derivative is selected from the group consisting of polyoxyethylene lauryl ether, polyoxyethylene cetyl ether, polyoxyethlene oleyl ether, polyoxyethylene higher alcohol ether, polyoxyethylene octyl phenyl ether and poly oxyethylene nonylphenyl ether.

5. The method according to claim 1, wherein the cholesterol esterase is derived from *Pseudomonas* sp.

6. The method according to claim 1, wherein said eliminating triglycerides to quantify triglycerides in low density lipoprotein further comprises a divalent metal ion selected from the group consisting of copper ion, iron ion, calcium ion and magnesium ion.

7. The method according to claim 6, wherein said divalent metal ion is selected from the group consisting of copper ion and iron ion.

8. The method according to claim 6, wherein said divalent metal ion is magnesium ion.

9. The method according to claim 1, wherein the quantifying triglycerides in low density lipoprotein exhibits a correlation coefficient of 0.856 to 0.977 with a quantification measurement of triglycerides in low density lipoprotein by an ultracentrifugation method.

* * * * *